(12) United States Patent
Smith et al.

(10) Patent No.: US 8,067,358 B1
(45) Date of Patent: Nov. 29, 2011

(54) TRIPLE-ACTION REMEDY FOR REMOVING TOXIC OILS FROM SKIN WITH SIMULTANEOUS SOOTHING AND HEALING

(75) Inventors: Robert Lee Smith, Corvallis, OR (US); John Mark Christiansen, Corvallis, OR (US); Wendy S Langley, Albany, OR (US); Vernon W. Smith, Albany, OR (US); Brian Chipman, Fairfield, CA (US)

(73) Assignee: Tec Laboratories, Inc., Albany, OR (US)

( * ) Notice: Subject to any disclaimer, the term of this patent is extended or adjusted under 35 U.S.C. 154(b) by 163 days.

(21) Appl. No.: 12/269,208

(22) Filed: Nov. 12, 2008

Related U.S. Application Data

(62) Division of application No. 11/091,328, filed on Mar. 28, 2005, now abandoned.

(51) Int. Cl.
*A61K 31/00* (2006.01)

(52) U.S. Cl. .......................................... 514/1; 514/862

(58) Field of Classification Search .................. None
See application file for complete search history.

(56) References Cited

U.S. PATENT DOCUMENTS 6,423,746 B1   7/2002   Yarbrough et al.

OTHER PUBLICATIONS

Tec Labs, Tecnu Extreme(R) Meidcated Poison Ivy Scrub, Apr. 1, 2002, printed from http://www.teclabsinc.com/products.cfm?id=710BAA10-0DF6-555C-F0B4010297877F77 on Oct. 29, 2010, 3 pages.*
Google.com, date confirmation of internet search entry of Tecnu Extreme(R) by Tec Labs (1), printed from http://www.google.com/search?sourceid=navclient&ie=UTF-8&rlz=1T4GGLD_en_US343&q=tecnu+ivy+scrub+&as_qdr=y15, 1 page.*
Google.com, date confirmation (2) of web page publication entry of Tecnu Extreme(R) on Apr. 1, 2002, printed from http://www.google.com/search?sclient=psy&hl=en&site=&source...&as_qdr=y15&cad=cbv, 1 page.*
Tec Labs, Tecnu Extreme(R) Medicated Poison Ivy Scrub label, 2009, printed from http://www.teclabsinc.com/drug_label/TecX_label.pdf on Oct. 29, 2010, 1 page.*
US2002/0183284A1, Dec. 5, 2002, Yarbrough, Urushiol-Induced Contact Dermatitis Solution.
U.S. Appl. No. 10/730,715, filed Dec. 8, 2003, "Compositions, Methods, and Kit for Removing Toxic Oils from Skin" assigned to Tec Laboratoies, Inc.
"Make your Own First-Aid Kit", www.herbsforhealth.com.
Herb Pharm Herbal Extracts, Grindelia Sassafras Compound, www.absolutelythepurist.com.
Herbs for Common Ailments, Allergy and Poison Oak, www.eurekanaturalfoods.com.
Summactin, product literature from web site www.sumactin.com.
Product Review on Sumactin from www.productreview.ws/poison-ivy.htm.

* cited by examiner

*Primary Examiner* — Sreeni Padmanabhan
*Assistant Examiner* — Gigi Huang

(57) ABSTRACT

Disclosed are formulae and methods for the simultaneous relief of a variety of unpleasant symptoms of poison ivy on the skin. The compositions of the present invention remove toxic urushiol, relieve itching of the skin from urushiol, and heal the dermatitis caused by urushiol. A preferred embodiment of the invention is a topical dosage form which can be applied as often as desired, may be scrubbed onto the skin, and leaves a soothing effect on the skin after rinsing with warm water.

4 Claims, No Drawings

TRIPLE-ACTION REMEDY FOR REMOVING TOXIC OILS FROM SKIN WITH SIMULTANEOUS SOOTHING AND HEALING

RELATED PATENT APPLICATIONS

This is a utility patent application that is a divisional of prior patent application Ser. No. 11/091,328 filed Mar. 28, 2005 that claims the benefit of provisional application No. 60/558,441 filed Apr. 1, 2004

FIELD OF THE INVENTION

The present invention relates to the removal of toxic plant oils from the skin. More specifically, the toxic plant oil removed is urushiol resulting from accidental contact with poison ivy, poison oak and sumac. The compositions of this invention remove urushiol from the skin while simultaneously relieving the itch caused by the contact and healing the dermatitis caused by the contact.

BACKGROUND AND RELATED ART

The oleoresin urushiol, which flows through the poison ivy plant and its relatives, causes an allergic reaction of a red, itchy rash. Urushiol is a sticky, clear oil containing catechols and other phenolic resins that act as a powerful hapten (a substance that does not stimulate antibody formation but reacts selectively in vitro with an antibody).

Urushiol resin remains stable, even in dead or dried plants, and therefore is equally hazardous in the winter as in the summer. Estimates state that 50-70% of the U.S. population is allergic to urushiol and would acquire the rash on casual contact. A person allergic to poison ivy is also allergic to poison oak and poison sumac. People may not be allergic to poison ivy the first time they touch it, but can become allergic as the skin sensitizes to the resin.

Treatments for removing toxic oils from skin are numerous and encompass quite a large variety of products. The current invention is a one-step treatment that not only removes urushiol from the skin but relieves the itch and soothes the skin in just one step. That step uses the unique ingredient, *Grindelia Robusta*, which is a homeopathic remedy. In this invention, *Grindelia* is compounded with a variety of other ingredients that are combined and formulated as a topical cleanser that is safe, effective, and easy to use.

Earlier poison ivy medicaments are formulated as multi-step products. Applicants have a pending application to a product called Ivy-Stat that is a two-component product wherein poison ivy is controlled by a kit where one component removes toxic oils from the skin and another component relieves and soothes the skin from residual itch and sensitivity. The instant invention has only one component.

Tec Labs, Inc., assignee of the present invention, is the owner of a known and currently manufactured product called Tecnu®. It is sold as an outdoor skin cleanser that removes the poison oak and ivy oil, urushiol, which causes rash and itching. Tecnu comprises deodorized mineral spirits, water, propylene glycol, octylphenoxy-polyethoxyethanol, mixed fatty acid soap, and fragrance.

The new topical remedy that is the subject of the instant invention contains at least one surfactant, a thickener, a preservative, an analgesic, a fragrance and a scrubbing agent. Preferred embodiments of the invention will be described in further detail in the detailed description section below.

Other than Tecnu, topical remedies that are commercially available at this time include soaps. Soaps may remove urushiol, but do nothing to relieve the itch or heal the rash that results from urushiol contact. The present invention removes the oil as well as relieves the itch and treats the rash simultaneously. The triple-action product is a new way to solve an old hard-to-solve problem of urushiol contact dermatitis. It is a one-step product that doesn't have to be mixed or formulated by a homeopath.

Another natural poison ivy remedy sold includes Sumactin, which contains jewelweed, aloe, plantain, and soapwort. The instant invention differs from Sumactin both in both composition and action. The Internet offers a plurality of products that are advertised and available as homeopathic remedies for urushiol contact. Applicants' invention comprises a triple-action, quality manufactured natural product which is not duplicated by web sites selling individual ingredients.

SUMMARY OF THE INVENTION

Disclosed herein are compositions that remove urushiol from the skin while simultaneously relieving skin irritation and fostering skin healing in one complete, water-based formula comprising a thickening agent, at least one surfactant, a topical analgesic, a preservative, at least one fragrance, and a scrubbing agent which, when formulated and used as a wash applied topically to skin that has been exposed to urushiol, removes said urushiol from the skin while simultaneously relieving the itch and healing irritation of the skin.

DETAILED DESCRIPTION OF PREFERRED EMBODIMENTS

As noted above, urushiol is the toxin responsible for the contact dermatitis caused by poison ivy, poison oak, and other urushiol-containing plants. When housed inside an unruptured plant leaf, urushiol is a light, colorless oil. The leaves are easily damaged by the slightest contact or even by a breeze. Therefore, it is rare to find a plant that does not have at least some ruptured leaves. When exposed to oxygen in the air, urushiol easily oxidizes and, after polymerizing, turns a blackish color.

The reaction experienced by most people is the result of exposure to the oleoresin containing the urushiol. The reaction is an allergic eczematous contact dermatitis characterized by redness, swelling, papules, vesicles, bullae, and streaking.

Applicants have surprisingly discovered that a composition containing up to about 1 weight percent of a thickening agent, up to about 35 weight percent of at least one surfactant, up to about 10 weight percent of a topical analgesic, up to about 0.3 weight percent of a preservative, up to about 1 weight percent of at least one fragrance, up to about 15 weight percent scrubbing agent; and the balance purified water which, when formulated and used as a wash applied topically to skin that has been exposed to urushiol, removes said urushiol from the skin while simultaneously relieving the itch caused by urushiol and healing skin irritation caused by it as well.

The composition may have as a thickening agent at least one material selected from the group consisting of agars, alcohols, algins, alkanolamides, aluminas, bentonite, betaines, carbomers, carrageenans, castor oil, cellulose, chlorides, cocamides (including cocoamide DEA), carboxyvinyl polymer, cocoa butter, cocoamines, coconut, copolymers, cornstarch, diethanolamides, gelatin, glutamates, glycerine, gums, hydroxypropyl methyl cellulose, linoleic diethanolamide, mica, myristates, palmitates, pectins, calendula, petrolatum, quarterniums, polyvinyl pyrrolidone, silica, silicates, silicons, sodium, soya, starches, stearates, sulfonates, triglycerides, and waxes, including their derivatives, ethers, esters, oils, extracts, and salts thereof. A particularly preferred thickening agent is cocoamide DEA, available from Stepan Chemical Company as Ninol.

The composition may have surfactants selected from the group consisting of alcohols, alkanolamides, alkanolamines, alkyl benzenes, olefins, acetates, oxides, amines, betaines, polymers, alkylphenols, fatty acids, phenols, glycols, imidazolines, isothionates, lanolin, lecithin, lignin, anhydrides, methyl esters, glycerides, sulfonates, glycols, phenols, polycyclic aromatic hydrocarbons, quaternary surfactants, sarconsines, silicone, soaps, sorbitan, sugars, oils, sorbates, polysorbates, octoxynols, nonoxynols, nonyl phenyl ethoxylates, sodium lauroyl sarcosinate, laureth-4 polyoxyethylene lauryl ether, (also known as (POE (4) laurel ether and sold by Uniquima as Brij® 30) and lanolin alcohol, including their derivatives, ethers, esters, sulfates, ethoxylates, oils, extracts, and salts. The surfactants of this invention can be thickening surfactants and/or non-ionic surfactants. Particularly preferred surfactants are Brij® 30 and polysorbate 20. Polysorbate 20, also known as Tween 20, supplied by Roche Applied Science, is Poly(oxyethylene)(20)-orbitane monolaurelate.

The composition may have at least one topical analgesic selected from the group consisting of benzocaine, butamben picrate, dibucaine, dibucaine hydrochloride, dimethisoquin hydrochloride, dyclonine hydrochloride, lidocaine, lidocaine hydrochloride, pramoxine hydrochloride, tetracaine, tetracaine hydrochloride, camphor, camphorated metacresol, juniper tar, menthol, phenol, phenolate sodium, resorcinol, diphenhydramine hydrochloride, triplennamine hydrochloride, hydrocortisone, hydrocortisone acetate, *arniflora arnica*, tea tree, witch hazel, allyl isothiocyanate, ammonia, methyl salicylate, terpentine, capsaicin, capsicum, capsicum oleoresin, histamine dihydrochloride, methyl nicotinate, cayenne, cinnamon, methylsulfonylmethane, aloe vera, comphrey, *Grindelia robusta*, ginger, lemongrass, jewelweed, guava, thyme, belladonna, wintergreen, clove, cinnamon, kava, allspice, turmeric, aconitum, mustard, hypericum, borax, calcium suphide, sarracenia, and eucalyptus, including their extracts, oils, and salts. In this invention, a preferred analgesic is *Grindelia robusta*.

The composition may have at least one preservative that is selected from the group consisting of benzethonium chloride, at least one alkyl paraben, benzalkonium chloride, methylbenzethonium chloride, hexylresourcinol, phenol, quaternary ammonium compounds, triclocarbon, triclosan, tea tree, grapefruit seed, thyme, calendula, oregano, orange, lemongrass, cinnamon, rose, clove, eucalyptus, peppermint, geranium, meadowsweet, anise, orris, mustard, rosemary, cumin, neroli, birch, lavender, melissa balm, ylang ylang, juniper, fennel, garlic, lemon, cajeput, sassafras, heliotrope, methylene blue, goldenseal, Oregon grape, sucrose, violet, pine, parsley, sulphur, benzoyl peroxide, chloroxylenol, ethanol, and isopropyl alcohol, including their extracts, oils, and salts. In this invention, a preferred preservative is benzethonium chloride.

The composition will contain at least one fragrance that is selected from the group consisting of menthol, peppermint, pine, lemon, lavender, tea tree oil, thyme, wintergreen, clove, cinnamon, allspice, eucalyptus, oregano, orange, rose, geranium, meadowsweet, anise, rosemary, ylang ylang, sassafras, Oregon grape, violet, lemongrass, and cinnamon. In the present invention, a preferred fragrance is pine.

Another ingredient of the claimed composition is an exfoliant or scrubbing agent. This ingredient is selected from the group consisting of polyethylene beads, polyethylene spheres, polyethylene granules, ground nut shells, ground fruit stones, hydrogenated vegetable oils, pumice, jojoba beads, jojoba prills, corundum crystals, sugar, oatmeal, salt, corn cob granules, plant seeds, milled adzuki beans, ground luffa, microwax meal beads, ground egg shell, styrene granules, sand, ceramic beads, glass beads, polypropylene beads, avocado prills, and alumina. In this invention, a preferred scrubbing agent is polyethylene beads.

The above ingredients are formulated into a triple-action cream that, when applied to skin that has been exposed to urushiol, acts as an exfoliant that decontaminates the exposed skin and removes the toxic oil therefrom. It also relieves the itch caused by urushiol and heals the dermatitis also caused by urushiol. It should be noted that while urushiol causes multiple symptoms to the skin it contacts, the present invention treats the same symptoms in one step with one composition.

Among the topical analgesics listed above is a natural product called *Grindelia*. It is also known as rosin wood or gum plant. It is found in a variety of habitats ranging from salt marsh and coastal scrub to desert and short-grass prairie.

*Grindelia robusta* is a biennial or perennial herb, which is sometimes woody at its base. The leaves are about 5 cm long, broadly spatulate near the bottom and sessile or clasping at the top. It has yellow flower heads that may be numerous and are hemispherical, 1 cm. broad. Flowering occurs in mid-summer to fall. The plant has a balsamic scent and a pungent, bitter taste.

Although known in the art as a natural remedy to urushiol, until this invention *Grindelia* has not been part of a triple-action mixture of ingredients. In a plurality of web sites, *Grindelia* is advertised as a poison ivy remedy. Included among the sites are of alyshebasoaps, herbs for health, eurekanaturalfoods, and absolutelythepurist. They advertise the *Grindelia* with and without other ingredients and in a variety of forms. The products are not advertised as triple-action products as is the present invention. As has been stated, these products are distinct from applicants' invention because in the composition of the instant invention, *Grindelia* keeps its activity, which is a triple-action product that removes urushiol, relieves itch, and heals the skin simultaneously. There is nothing else required for the user to buy, apply, or use.

Furthermore, the composition of this invention is non-toxic and safe to use repeatedly. It comprises formulations that are non-toxic to humans and household pets but are effective in removing toxic oils such as urushiol from skin. The products of this invention are manufactured by a company that uses quality assurance and stands behind the product. This is also a distinction from many of the on-line *Grindelia* product offerings The following is a description of a laboratory process used to synthesize a quantity of triple-action cream of the present invention:

EXAMPLE 1

To 52 grams of purified water was added 1 gram of carboxyvinyl polymer (Carbopol®) thickening agent. The combination was mixed slowly. To it, with continued mixing, was added 14 grams of surfactant Brij 30, polyoxyethylene lauryl ether and 14 grams of surfactant Tween 20, polysorbate 20. Along with Brij 30 were added 1 gram of thickening surfactant Ninol®, coconut diethanolamide.

While mixing continues, 10 grams of topical analgesic *Grindelia Robusta* extract 2× was added. At this point 0.15 grams of benzthonium chloride was added with a rapid mixing speed. The last ingredients added are 7.8 grams of polyethylene beads and 0.05 grams of fragrance. A preferred fragrance added here is PineFresh® fragrance, made by the Bell Company.

Packaging and quality assurance procedures are in place to assure product safety and customer satisfaction at all times.

The triple-action composition of this invention may be supplied in a variety of forms. Examples include creams, ointments, gels, lotions, solutions, sprays, or foams that can work when rubbed directly into the skin rash.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

What is claimed is:

1. A method for removing urushiol from a person's skin while simultaneously relieving and healing contact dermatitis associated with urushiol contact comprising the steps of
   i) firstly applying to the exposed skin a composition made by combining:
      a) three surfactants consisting of about 14 weight percent of polysorbate 20, and about 14 weight percent of polyoxyethylene (4) lauryl ether, and about 1 weight percent of coconut diethanolamide;
      b) a thickening agent consisting of about 1 weight percent of a so carbomer;
      c) a preservative consisting of about 0.15 weight percent of benzethonium chloride;
      d) a topical analgesic consisting of about 10 weight percent of *grindelia robusta* extract;
      e) an inert scrubbing medium consisting of about 7.8 weight percent polyethylene beads;
      f) about 0.5 weight percent of at least one fragrance; and
      g) about 52 weight percent purified water; in a form allowing for application to skin; followed by
   ii) secondly cleansing the skin by rubbing the composition into the affected area; followed by
   iii) thirdly rinsing the affected area with water to clean away dead skin and debris;
resulting in finally leaving the person's skin free of urushiol whilst soothing said skin.

2. The method of claim 1 wherein the desired result, leaving the person's skin free of urushiol, is initiated by the person applying the composition to irritated skin.

3. The method of claim 1 wherein the composition is able to be scrubbed onto the skin before rinsing with water.

4. The method of claim 1 wherein the composition is able to be applied as many times as desired following the initial application until the symptoms of contact dermatitis are relieved.

* * * * *